United States Patent
Peake, III

(10) Patent No.: US 10,949,568 B1
(45) Date of Patent: Mar. 16, 2021

(54) SYSTEMS AND METHODS FOR DISTRIBUTED, STATELESS, AND PERSISTENT ANONYMIZATION WITH VARIABLE ENCODING ACCESS

(71) Applicant: Illuscio, Inc., Culver City, CA (US)

(72) Inventor: William Peake, III, Los Angeles, CA (US)

(73) Assignee: Illuscio, Inc., Culver City, CA (US)

( * ) Notice: Subject to any disclaimer, the term of this patent is extended or adjusted under 35 U.S.C. 154(b) by 0 days.

(21) Appl. No.: 17/079,932

(22) Filed: Oct. 26, 2020

(51) Int. Cl.
*G06F 21/62* (2013.01)
*G16H 10/60* (2018.01)
*G06F 16/11* (2019.01)
*G06F 16/14* (2019.01)

(52) U.S. Cl.
CPC ........ *G06F 21/6254* (2013.01); *G06F 16/116* (2019.01); *G06F 16/152* (2019.01); *G16H 10/60* (2018.01)

(58) Field of Classification Search
CPC .......... G06F 21/32; G06F 21/64; G06F 16/13; G06F 16/93; G06F 16/9535; G06F 21/62; G06F 40/166; G06F 21/554; G06F 2211/008; G06F 2221/2151; G06F 16/1873
See application file for complete search history.

(56) References Cited

U.S. PATENT DOCUMENTS

| | | | | |
|---|---|---|---|---|
| 9,659,062 | B1 * | 5/2017 | Kapoor | G06F 16/24564 |
| 2006/0294127 | A1 * | 12/2006 | Nettles | G06F 15/16 |
| 2009/0083372 | A1 * | 3/2009 | Teppler | G06F 15/16 |
| | | | | 709/203 |
| 2013/0311772 | A1 * | 5/2012 | Etheridge | H04L 9/32 |
| | | | | 713/156 |

* cited by examiner

*Primary Examiner* — Angelica Ruiz
(74) *Attorney, Agent, or Firm* — Ansari Katiraei LLP; Arman Katiraei; Sadiq Ansari

(57) ABSTRACT

Provided is an anonymization system for performing distributed, stateless, and persistent anonymization of with variable encoding. The anonymization system may receive a first file with at least a first data element. The first data element may include a tag and restricted data. The anonymization system may change a first encoding of the tag having a first size to a second encoding having a second size that is smaller than the first size. The anonymization system may replace the restricted data with different anonymized data based on a persistent mapping of the restricted data to the anonymized data, and may output the first data element with the second encoding of the tag and the anonymized data to a database or an anonymized second file.

21 Claims, 8 Drawing Sheets

SYSTEMS AND METHODS FOR DISTRIBUTED, STATELESS, AND PERSISTENT ANONYMIZATION WITH VARIABLE ENCODING ACCESS

BACKGROUND

Health Insurance Portability and Accountability Act ("HIPAA") compliant systems, advertisers, real-time traffic systems, and/or other systems may access files that contain private, confidential, and/or restricted data. To ensure compliance with any regulations and/or prevent exposure of the data, the data within the files may be anonymized or deidentified to remove or replace the private, confidential, and/or restricted data prior to the systems accessing the files and/or the data of the files.

DETAILED DESCRIPTION OF PREFERRED EMBODIMENTS

The following detailed description refers to the accompanying drawings. The same reference numbers in different drawings may identify the same or similar elements.

Provided are systems and methods for distributed, stateless, and persistent anonymization with variable encoding access. In some embodiments, the distributed, stateless, and persistent anonymization may include dynamically scaling resources of an anonymization system to provide parallel, out-of-order, and/or real-time data anonymization for a particular related set of files. In some embodiments, the distributed, stateless, and persistent anonymization may include providing data persistence across the anonymized data such that relationships (e.g., contextual, temporal, etc.) between static or changing data in the related set of files is preserved despite the data being anonymized. The anonymization system may preserve the relationships and provide data persistence even when the data of different files are anonymized by different agents, at different times, and/or using different anonymization passes. For instance, the anonymization system may use the same anonymized data to replace first static data when anonymizing a first file on a first day and when anonymizing a different second file on a second day during an entirely different anonymization pass. Similarly, the anonymization system may replace temporal data that changes in different files with fuzzed anonymized values that preserve relative temporal relationships across the anonymized temporal data with slightly different offsets. The slightly different offsets of the fuzzed anonymized values may prevent a bad actor from reversing the anonymization in attempts to obtain the original time values across the sequence of related files.

The anonymization system may use the variable encoding to reduce the size of the data and/or the tags that identify the data prior to and after anonymization. By reducing the size of the data and/or tags, the anonymization system may allow for faster transfer of the anonymized data across a data network, faster anonymization of the original data, and/or faster access to the original and/or anonymized data as a result of reducing the size of the tags that identify the data.

Figure 1:
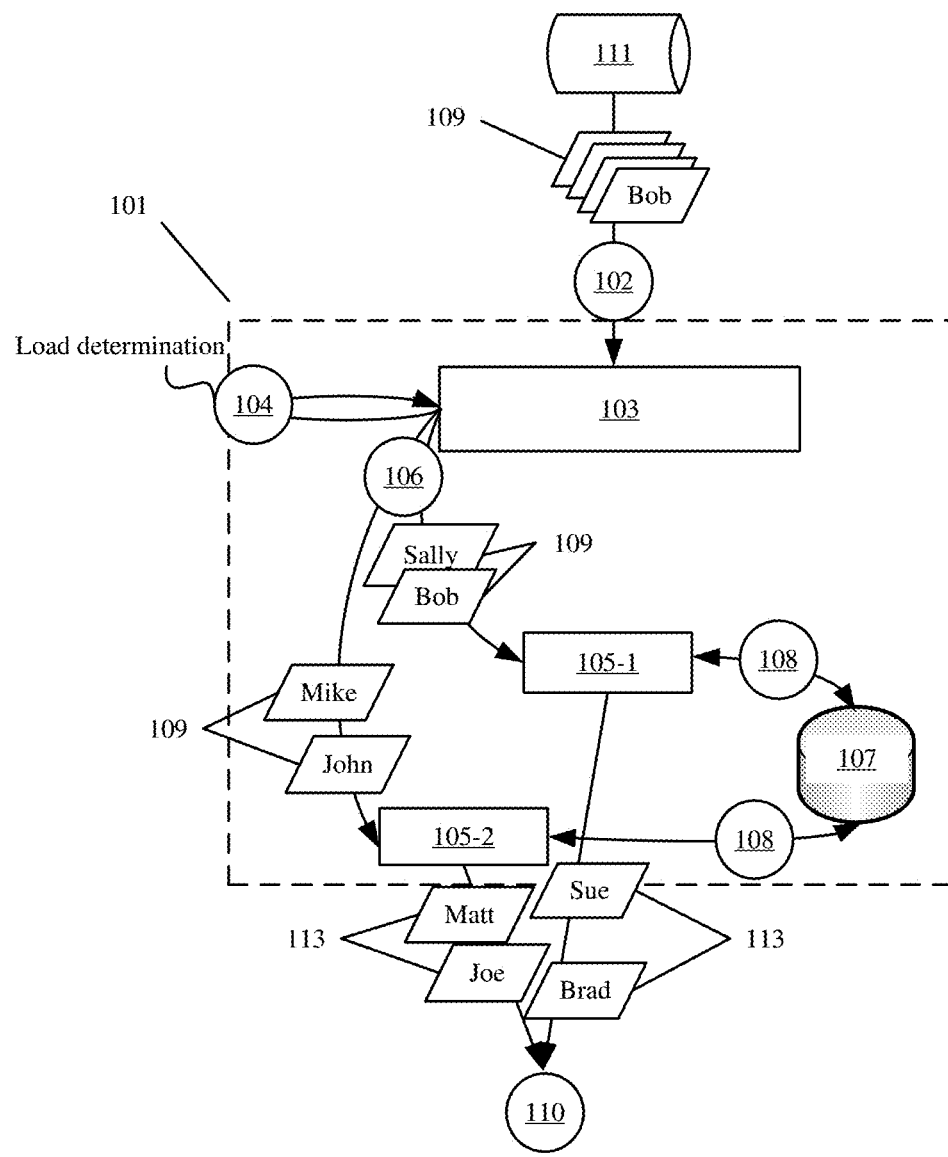
FIG. 1 an example of distributed, stateless, and persistent data anonymization in accordance with some embodiments presented herein.

FIG. 1 an example of distributed, stateless, and persistent data anonymization in accordance with some embodiments presented herein. The distributed, stateless, and persistent data anonymization is performed by anonymization system 101 of some embodiments. As shown in FIG. 1, anonymization system 101 may include controller 103, a set of anonymization agents 105, and database 107.

Controller 103 may coordinate and control the distributed operation of anonymization agents 105 in response to receiving (at 102) one or more related files 109 for anonymization or deidentification from one or more data sources 111. Files 109 may be related by virtue of providing different data for the same entity (e.g., the same patient), object, event, condition, and/or other commonality in files 109. In other words, files 109 may capture and/or include data that is temporally related, contextually related, and/or related due to some other relationship for commonality within files 109.

Data sources 111 may include devices, systems, and/or entities that generate and/or store files 109 with private, confidential, and/or restricted data. For instance, data sources 111 may include hospitals, imaging systems (e.g., Magnetic Resonance Imaging ("MRI") devices, Positron Emission Tomography ("PET") scanning devices, Computerized Tomography ("CT") scanning devices, etc.), and wireless telecommunications providers, advertisers, and/or others that originate and/or host private, confidential, and/or restricted data.

In some embodiments, controller 103 and/or anonymization system 101 may be integrated with or directly connected to data sources 111. In some other embodiments, controller 103 and/or anonymization system 101 may be communicably coupled to data sources 111 via a data network, and may receive one or more files 109 over the data network.

In response to receiving (at 102) files 109, controller 103 may determine (at 104) a load associated with anonymizing files 109. The load determination may be based on the number of files 109 that are pending anonymization. In particular, the load determination may be based on the size of files 109 and/or the amount of data in each file 109 pending anonymization.

Controller 103 may instantiate (at 106) one or more anonymization agents 105 to perform the distributed, stateless, and persistent anonymization of files 109 based on the load determination. For instance, controller 103 may instantiate (at 106) a different anonymization agent 105 for every five files in the received set of files 109, and controller 103 may perform a round-robin or other assignment of files 109 until each anonymization agent 105 has five files to anonymize. In some embodiments, instantiating (at 106) an anonymization agent 105 may include allocating cloud computing resources (e.g., processor, memory, networking, and/or other resources), deploying an executable image of an anonymization agent 105 to the allocated resources, configuring the image to retrieve one or more files 109 and/or persistent anonymization data from database 107, and/or controlling the instantiated anonymization agent 105 in anonymizing the data of the one or more retrieved files 109. In some other embodiments, instantiating (at 106) an anonymization agent 105 may include forking or creating a new thread, process, or application, and configuring the new thread, process, or application to perform the distributed, stateless, and persistent anonymization of data for one or more assigned files 109.

As shown in FIG. 1, controller 103 may instantiate (at 106) two anonymization agents 105-1 and 105-2 (sometimes collectively referred to as "anonymization agents 105" or individually as "anonymization agent 105"), and may distribute half of files 109 to first anonymization agent 105-1 and the other half of files 109 to second anonymization agent 105-2. In some embodiments, controller 103 may distribute files 109 out-of-order or out-of-sequence to each of anonymization agents 105-1 and 105-2. In other words, controller 103 may assign a first file and a fourth file from files 109 to the first anonymization agent 105-1, and a second file and a third file from files 109 to the second anonymization agent 105-2.

Each anonymization agent 105 may load at least one file 109 into memory, may scan file 109 for private, confidential, and/or restricted data types, may replace (at 108) data for the private, confidential, and/or restricted data types with persistent anonymized data from database 107, and may output (at 110) anonymized files 113 comprising original unrestricted data from files 109 and anonymized and/or deidentified data for restricted data from files 109. Anonymization agents 105 may output (at 110) anonymized files 113 to one or more devices, systems, and/or entities that do not have access or are not authorized to access the private, confidential, and/or restricted data, but may use the anonymized data from anonymized files 113 without restriction or concern of violating privacy, confidentiality, and/or other data use restrictions. In some embodiments, controller 103 may collect anonymized files 113 that are output (at 110) from anonymization agents 105, and may provide anonymized files 113 in response to requests from the one or more devices, systems, and/or entities that do not have access or are not authorized to access the private, confidential, and/or restricted data. For instance, a content and/or service provider may represent data source 111, and may have location, identification, and/or other information about its users. The content and/or service provider may use anonymization system 101 to anonymize the identification and/or other information about its users, but still provide location information to advertisers that can then provide geographically relevant advertising content to the user without violating user privacy.

By instantiating two or more anonymization agents 105, anonymization system 101 may perform a distributed, parallel, and/or out-of-order anonymization of the data from set of related files 109. The distributed, parallel, and/or out-of-order anonymization of the data may facilitate real-time data anonymization by having anonymized data for a next file ready as the anonymized data of an earlier file is accessed.

Database 107 may provide a central repository for mapping the same private, confidential, and/or restricted static data in original files 109 to the same anonymized data in anonymized files 113, and for tracking the offsets and/or fuzz criteria that is used to persistently anonymize private, confidential, and/or restricted data that changes in original files 109. By referencing the mappings, offsets, and/or fuzz criteria in database 107, different anonymization agents 105 may anonymize data from different files of related set of files 109 at the same time, in parallel, and/or at different times, and may maintain persistency between the anonymized data in resulting anonymized files 113 despite using different anonymization agents 105 to anonymize the data from original files 109 at the same time, at different times, or out-of-order. Since the mapping, offsets, and/or fuzz criteria is maintained in and/or managed by database 107, anonymization agents 105 may operate in a stateless manner. In particular, the operation, output, anonymization, and/or other state of one anonymization agent 105 may have no effect on the operation, output, anonymization, and/or other state of another anonymization agent 105.

Figure 2:
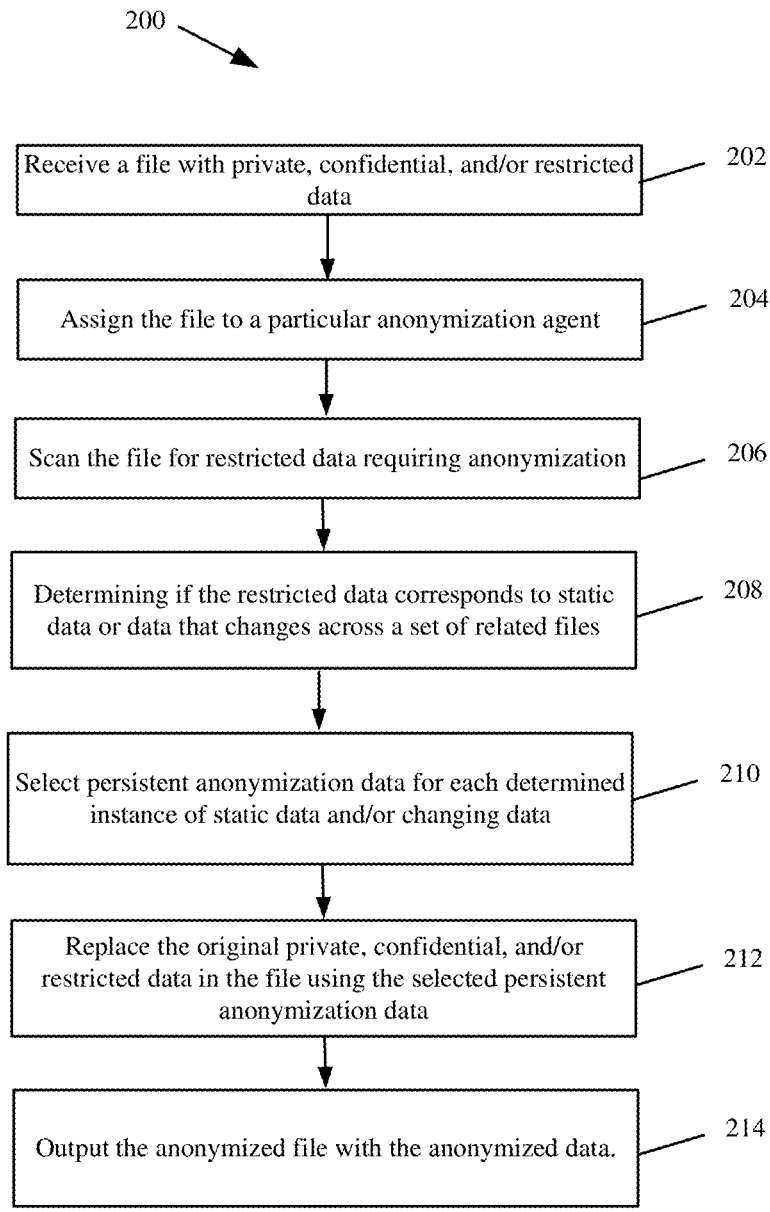
FIG. 2 presents a process for performing the distributed, stateless, and persistent data anonymization in accordance with some embodiments presented herein.

FIG. 2 presents a process 200 for performing the distributed, stateless, and persistent data anonymization in accordance with some embodiments presented herein. Process 200 may be performed by one or more components of anonymization system 101.

Process 200 may include receiving (at 202) a file with private, confidential, and/or restricted data. For instance, the file may include a Digital Imaging and Communications in Medicine ("DICOM") file that stores a medical image or scan for a patient, and that includes a header and/or metadata storing the patient name, patient identifier, name, sex, age, hospital name, patient condition, physician name, procedure, and/or other private, confidential, and/or restricted data that violates the Health Insurance Portability and Accountability Act ("HIPAA") regulation and/or other regulations if used or accessed by unauthorized parties. In some embodiments, controller 103 may receive or may pull the file from one or more data sources 111 in response to a request from a device, system, and/or entity that is not authorized to access the restricted data of the file, wherein the request is directed to anonymization system 101 and/or is a request to access the unrestricted data and anonymized data for the restricted data of the file. The request may be issued as a HyperText Transfer Protocol ("HTTP") GET request, a Distributed File System ("DFS") request, a gRPC remote procedure call, and/or other requests for accessing the file and/or the anonymized instance of the file over a data network. The request may include a Uniform Resource Locator ("URL") that identifies the path and/or name of the file.

Process 200 may include assigning (at 204) the file to a particular anonymization agent 105. Controller 103 may assign (at 204) the file based on overall load and/or availability of the particular anonymization agent 105.

Process 200 may include scanning (at 206) the file for restricted data requiring anonymization. In some embodiments, anonymization system 101 and/or anonymization agents 105 may be configured to detect restricted data from restricted data type definitions and/or data formats. For instance, a DICOM file may be defined according to the DICOM file format, and the DICOM file format may define the formatting for specific restricted data types. In some embodiments, the data types may be defined as key-value pairs, and the restricted data types may be identified by a specific set of keys. In some embodiments, the data types may be defined with a particular string and/or value format, and the restricted data types may be identified using one or more regular expressions that correspond to the particular string and/or value format for one or more of the confidential data types. For instance, anonymization system 101 may be configured to anonymize a name data type regardless of the actual name or value in the file for that name data type. Anonymization system 101 may identify the name data type anywhere in a file header, metadata, and/or other data as a string starting with a capital letter, a set of lower-case letters, a space, a capital letter, and another set of lower-case letters.

In response to detecting data that should be anonymized, process 200 may include determining (at 208) if the restricted data corresponds to static data or data that changes across a set of related files. The determination (at 208) may be based on the file format definition and/or parameters that indicate whether the data for a particular data type is static or variable in a set of related files.

Static data may include a key-value pair, identifier, value, and/or other data that is constant throughout the set of related files. For instance, the same patient name or the same patient identifier used within the set of related files may correspond to static data. Anonymization system 101 may use the same anonymized data to persistently replace the static data. For instance, the same anonymized name may be used to replace every instance the original patient name is found in the set of related files. Anonymization system 101 may store a single mapping of particular anonymized data to particular static data, and may use the single mapping to replace all instances of the particular static data in each of the set of related files.

Changing data may include a particular key, field, identifier, and/or other data for a data type that has different values associated with it in the set of related files. A timestamp for when a file was created or an image was taken may correspond to changing data. The differences in the values may have significance. For instance, the differences in the values may serve as a measure of time, change, rate, improvement, and/or other relationships for the data in the set of related files. Anonymizing the changing data by simply replacing the values with randomized values may result in the relationships being lost, and a loss of significance in the other file data. Accordingly, anonymization system 101 may use the same offset or a common formula to anonymize the changing data and to retain persistence between the data by preserving the relationships in the changing data despite changing the actual data values.

Process 200 may include selecting (at 210) persistent anonymization data from database 107 for each determined (at 208) instance of static data and/or changing data in the received file that is subject to anonymization. Selecting (at 210) the persistent anonymization data may include querying database 107 with a unique signature that is derived from the file data and/or filename. For instance, a hash of a patient name and/or patent identifier may be used to select (at 210) a mapping from the static restricted data to anonymized data, an offset that is used to anonymize particular changing data in the set of related files, and/or fuzz criteria by which to obfuscate the offset that is used.

In some embodiments, database 107 may store the persistent anonymization data once it is generated for use in anonymizing particular restricted data for a first file in a set of related files by first anonymization agent 105-1 so that the same persistent anonymization data may be reused to anonymize other instances of the particular restricted data that are found in subsequent files and/or by other anonymization agents 105. In some other embodiments, database 107 and/or anonymization agents 105 may dynamically generate the persistent anonymization data for a set of related files if the persistent anonymization data does not already exist. For instance, the unique signature derived from the patient name and/or other static data in a set of related files may serve as a seed value for persistently generating the mappings, offsets, and/or fuzz criteria for different restricted data in the set of related files.

Generating a persistent mapping for particular data, such as a patient's name, may include determining if a mapping exists in database 107 for that name or a hash of the name. If no mapping exists, database 107 may map the name to a different anonymized name. For instance, anonymization system 101 may download and/or store a third-party name directory, and may use a hash of a patient's name to persistently identify an entirely different name from the name directory. Database 107 may store the mapping so that a query of the patient name or hash of the patient name may directly return the anonymized name every time. Alternatively, the patient's name may be hashed each time in order to persistently identify the same anonymized name. For other static data or data types, anonymization system 101 may use a random generator to produce an anonymized string or value, and may store a mapping of the anonymized string or value for the static data or data type in database 107 so that subsequent instances of the static data may be replaced using the same randomly generated anonymized string or value based on the mapping stored in database 107.

For changing data, database 107 may store a persistent offset or may dynamically generate a persistent offset for anonymizing data that changes across a related set of files. The changing data may correspond to temporal, incremental, state, and/or conditional data in which a previous value in a first file is relevant or related to a next value in a second file. For instance, the related set of files may include a set of medical scans of a patient, and the changing data may include times or dates when each scan was taken. In some embodiments, anonymization agent 105 may use the unique signature of the patient (e.g., hash of one or more of the patient name, the patient data of birth, institution identifier, etc.) to retrieve (at 210) the offset for persistently anonymizing the time or date field. For instance, the offset may specify moving the time in each file of the set of related files ahead by 5 hours. Accordingly, the time may be anonymized in each file of the set of related files while the relative relationships between the timing in the files is preserved. Therefore, if the timing information is relevant to determine the speed of a growth, recovery, and/or other change in the scans, the anonymized timing data preserves the relationship while hiding the actual time at which the scans were taken.

When the same offset is applied to particular data of a set of related files, it may be possible for a bad actor to reverse the offset and to determine the original values for the particular data from the set of related files via unauthorized access to the original value of the particular data from one file. Accordingly, database 107 may store different fuzz criteria for the offset of each set of related files. The fuzz criteria may provide additional differentiation in the data that is anonymized with an offset without invalidating the persistency and/or relationship between the anonymized data in the set of related files. For instance, the fuzz criteria may include a range that is a fractional amount of the offset. More specifically, for an offset of 5 minutes, the fuzz criteria may specify an additional offset ranging between a 5 second increase or decrease of the anonymized value. Accordingly, anonymization system 101 via one or more anonymization agents 105 may offset a particular time field in a first file of a set of related files by exactly 5 minutes (e.g., adding 5 minutes to the original time), may offset the particular time field in a second file of the set of related files by 4 minutes and 57 seconds (e.g., adding 5 minutes to the original time and then decreasing the resulting time by 3 seconds based on the specified range for the fuzz criteria), and may offset the particular time field in a third file of the set of related files by 5 minutes and 4 seconds (e.g., adding 5 minutes to the original time and then increasing the resulting time by 4 seconds based on the specified range for the fuzz criteria). Accordingly, the fuzz criteria may add randomness to the offset without invalidating the persistency and/or relationship in the particular time field across the set of related files.

Process 200 may include replacing (at 212) the original private, confidential, and/or restricted data in the file using the selected persistent anonymization data. In particular, anonymization agent 105 may replace each of the static data and/or changing data in the file, while preserving other original data that is not considered private, confidential, and/or restricted, and therefore not subject to anonymization. For instance, anonymization agent 105 may replace the patient name and/or identifier, hospital name and/or identifier, timestamp, procedure identifier, and/or other restricted data from a DICOM image, while leaving the DICOM image data and/or other unrestricted data in the file header and/or metadata intact (e.g., file size, image resolution, image properties, physician notes, etc.).

Process 200 may include outputting (at 214) the anonymized file with the anonymized data. Outputting (at 214) the anonymized file may include writing the anonymized file with the anonymized data to a storage device and/or transferring the anonymized file over a data network to a requestor or destination.

Figure 3A:
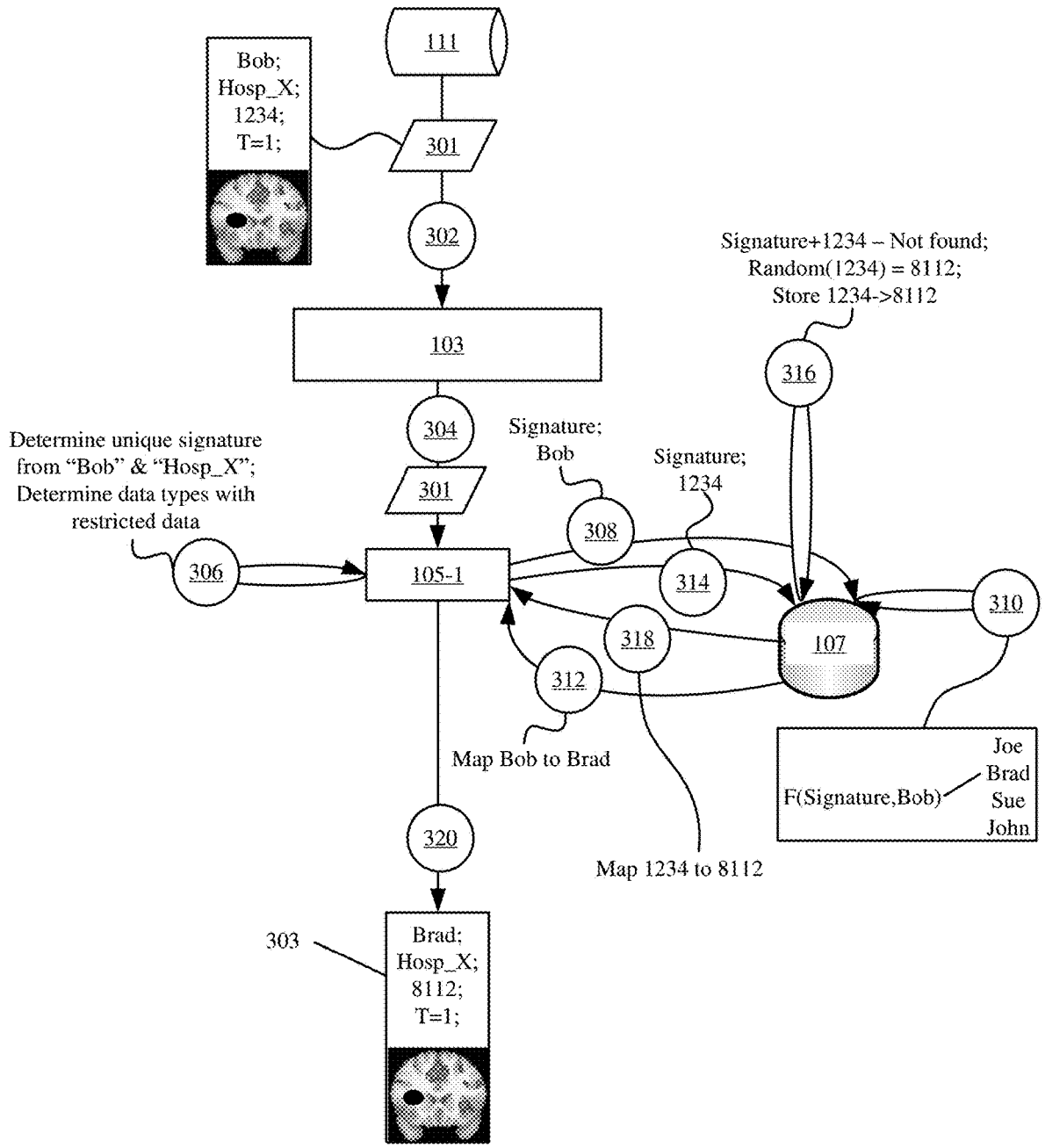
FIGS. 3A and 3B illustrate an example for stateless anonymization of static data in related files in accordance with some embodiments presented herein.
Figure 3B:
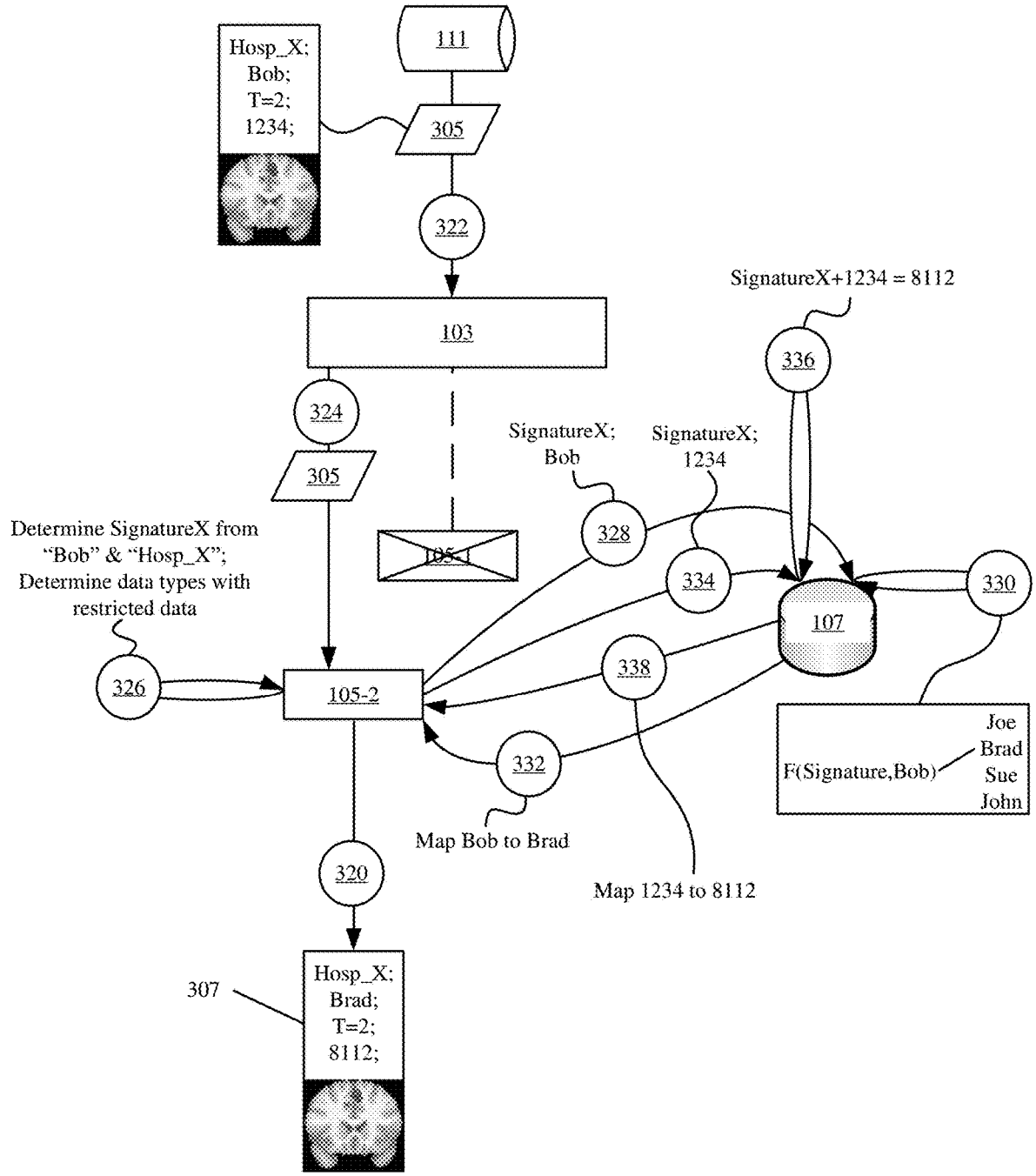

FIGS. 3A and 3B illustrate an example for stateless anonymization of static data in related files in accordance with some embodiments presented herein. As shown in FIG. 3A, controller 103 may receive (at 302) first file 301 from a set of related files at a first time. For instance, the first time may correspond to the time at which a first scan for a particular patient is generated. Controller 103 may assign (at 304) first file 301 to first anonymization agent 105-1 for anonymization.

First anonymization agent 105-1 may scan (at 306) first file 301 to determine a unique signature from the file data. In this case, the unique signature may be derived from hashing the patient name and the hospital identifier.

First anonymization agent 105-1 may also scan (at 306) first file 301 to identify a set of data types in first file 301 that contain restricted data that is subject to anonymization. In particular, first anonymization agent 105-1 may use one or more regular expressions to identify fields corresponding to the patient name, patient medical record number, age, date of birth, and/or other information regardless as to whether those fields are found in the same header, metadata, and/or file position and regardless as to whether those fields are present in the same order in different files.

First anonymization agent 105-1 may query database 107 with the unique signature to obtain persistent anonymization data for each of the anonymization targeted fields. Specifically, first anonymization agent 105-1 may issue one or more queries to database 1087, and each query may include the unique signature of first file 301 and the restricted data from at least one the identified fields that are subject to anonymization (e.g., patient name, patient medical record number, age, date of birth, and/or other data).

As shown in FIG. 3A, first anonymization agent 105-1 may perform (at 308) a first query using the unique signature and the actual patient name. Database 107 may persistently map (at 310) the unique signature and/or actual patient name to the same particular anonymized name in a list of anonymized names by hashing the unique signature and/or actual patient name, and by using the hash result to select the particular anonymized name in the list of anonymized names. In other words, the hash result for subsequent queries with the unique signature and the actual patient name may persistently select the particular anonymized name from the list of anonymized names.

Alternatively, database 107 may determine that an entry mapping the unique signature and the actual patient name to the particular anonymized name does not exist, and may use a random string generator to generate (at 310) the anonymized name. Database 107 may then create and/or store the mapping between the particular anonymized name and the combination of the unique signature and the actual patient name so that subsequent queries for the actual patient name or the unique signature and the actual patient name return the same anonymized name.

Database 107 may return (at 312) the particular anonymized name to first anonymization agent 105-1 in response to the first query. First anonymization agent 105-1 may replace the actual patient name in first file 301 with the anonymized name.

First anonymization agent 105-1 may perform (at 314) a second query using the unique signature and the patient medical record number or other static data. Database 107 may not store a mapping for the patient medical record number of the particular patient at the time of the second query. Database 107 may generate (at 316) an anonymized patient medical record number in the same format (e.g., same number of alphanumeric characters) as the original patent medical record number. In some embodiments, database 107 may scramble and/or rearrange the numbers of the patient medical record number to generate the anonymized patient medical record number, may use a random number generator to produce an entirely random value for the anonymized patient medical record number, and/or may use a mathematical to produce the anonymized medical record number from the original patient medical record number. Since a different anonymized medical record number is generated each time the unique signature and patient medical record number is provided, database 107 may create an entry that stores the mapping between the original patient medical record number and the generated anonymized patient medical record number. By storing the mapping, database 107 is able to use different random numbers, rather than a static value or formula, to generate anonymized medical record numbers for different patients.

Database 107 may provide (at 318) the anonymized patient medical record number to first anonymization agent 105-1 in response to the second query, and first anonymization agent 105-1 may replace the original patient medical record number in first file 301 with the anonymized patient medical record number.

First anonymization agent 105-1 may continue querying database 107 until each of the identified fields containing data that is subject to anonymization is replaced with persistent anonymized data. After anonymizing first file 301, first anonymization agent 105-1 may write, store, transfer, and/or otherwise output (at 320) anonymized first file 303, and first anonymization agent 105-1 may terminate. Terminating first anonymization agent 105-1 may include freeing or reallocating compute resources used by anonymization agent 105-1, and/or removing the anonymization agent instance that executes first anonymization agent 105-1 on a set of shared compute resources. In some embodiments, first anonymization agent 105-1 may output (at 320) anonymized first file 303 to database 107, database 107 may store contents (e.g., original data and/or anonymized data) of anonymized first file 303, and may index the data to allow for users to query and/or access the anonymized data directly from database 107.

FIG. 3B illustrates operation of anonymization system 101 at a later second time that may be minutes, hours, or days after the first time. At the second time illustrated in FIG. 3B, controller 103 may receive (at 322) second file 305 for anonymization, and may assign (at 324) second file 305 to second anonymization agent 105-2.

Second anonymization agent 105-2 may scan (at 326) second file 305 to determine a unique signature from the file data. In this case, the unique signature of second file 305 matches the unique signature of first file 301 due to second file 305 containing the same patient name and hospital identifier as first file 301. The same unique signature may indicate that second file 305 is related to first file 301, and/or that first and second files 301 and 305 are part of the same sequence or file set. For instance, second file 305 may include a second medical scan for the same patient with a first medical scan stored in first file 301.

Second anonymization agent 105-2 may scan (at 326) second file 305 to identify a set of data types in second file 305 that contain restricted data that is subject to anonymization. Second anonymization agent 105-2 may detect that second file 305 contains the patient name, patient medical record number, age, date of birth, and/or other information in a different order and/or placement than first file 301, and that these data types require anonymization.

Second anonymization agent 105-2 may query (at 328) database 107 with a first query using the unique signature and the patient name. As before, database 107 may not store a mapping between the actual patient name and the previously used particular anonymized name. However, database 107 may hash the unique signature and/or actual patient name in order to persistently identify (at 330) the particular anonymized name that was used to replace the actual patient name in first file 301. Accordingly, database 107 may return (at 332) the particular anonymized name to second anonymization agent 105-2 in response to the first query, and second anonymization agent 105-2 may persistently replace the actual patient name in second file 305 with the same particular anonymized name that was used in first file 301 for the same particular patient. The patient name replacement therefore occurs in a stateless manner without second anonymization agent 105-2 being dependent on any operations performed by first anonymization agent 105-1.

Second anonymization agent 105-2 may query (at 334) database 107 with a second query using the unique signature and the patient medical record number. In this instance, database 107 may determine (at 336) that a stored mapping exists between the patient medical record number of the particular patient and/or unique signature, and an anonymized medical record number that was previously used in first file 301 for the particular patient. Accordingly, database 107 may provide (at 338) the anonymized medical record number to second anonymization agent 105-2 without generating a new anonymized medical record number for second file 305. Second anonymization agent 105-2 may perform a persistent and stateless replacement of the original patient medical record number with the anonymized medical record number in second file 305.

Second anonymization agent 105-2 may continue querying database 107, and may continue performing the persistent and stateless replacement until each of the identified fields containing data that is subject to anonymization is replaced with persistent anonymized data. After anonymizing the restricted data of second file 305, second anonymization agent 105-1 may write, store, transfer, and/or otherwise output (at 340) anonymized second file 307, and second anonymization agent 105-2 may terminate operation. In some embodiments, second anonymization agent 105-2 may output (at 340) anonymized second file 307 to database 107, database 107 may store contents (e.g., original data and/or anonymized data) of anonymized second file 307 with the contents of anonymized first file 303 so that users may query and/or access the collective anonymized data from anonymized first file 303, anonymized second file 307, and/or other anonymized files in the same set of related files directly from database 107.

Figure 4:
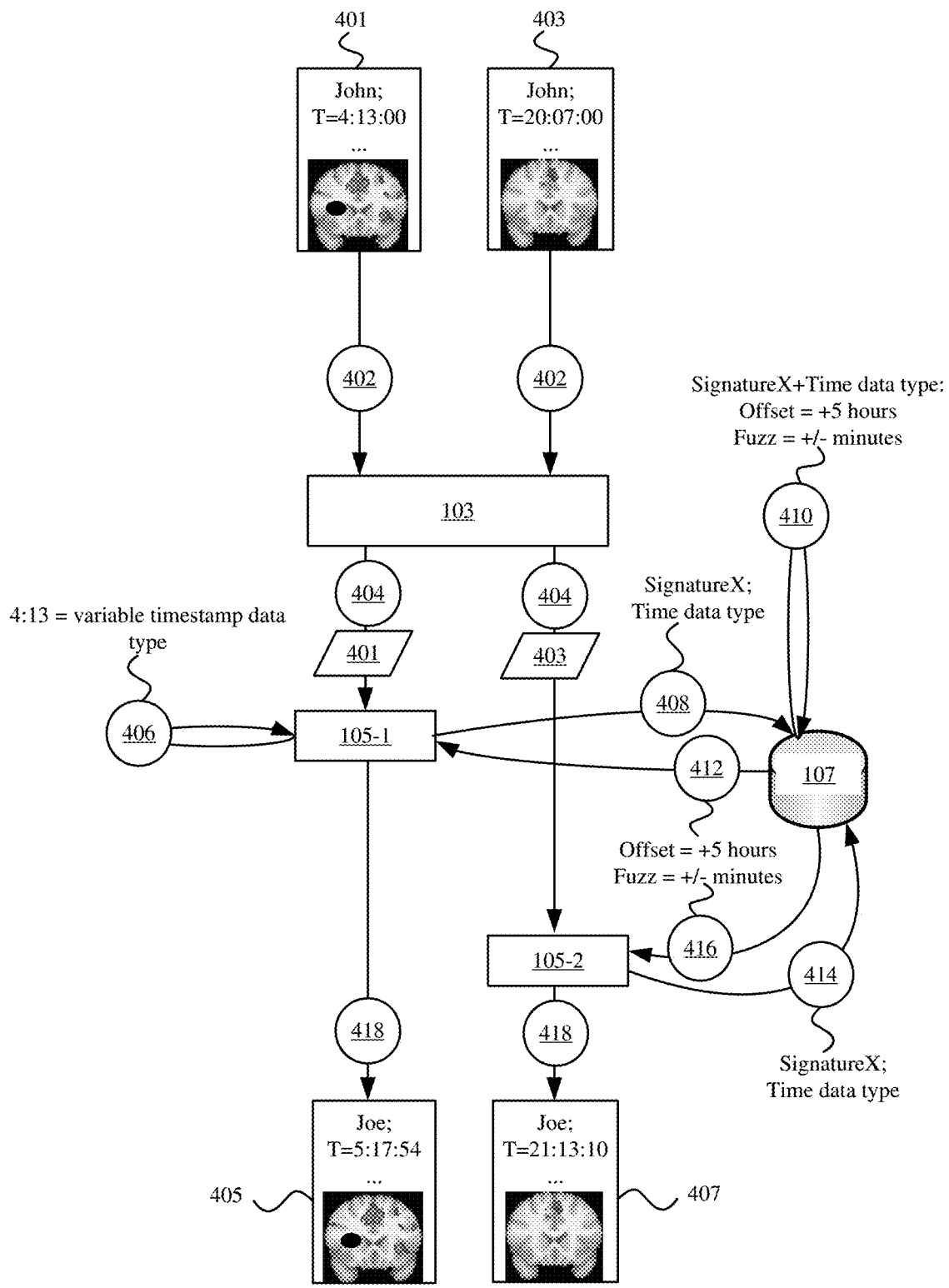
FIG. 4 illustrates an example for persistently anonymizing changing data to maintain data relationships while preserving anonymization integrity in accordance with some embodiments presented herein.

FIG. 4 illustrates an example for persistently anonymizing changing data to maintain data relationships while preserving anonymization integrity in accordance with some embodiments presented herein. FIG. 4 illustrates controller 103 receiving (at 402) first file 401 and second file 403 that are part of the same set of related files (e.g., files that are generated with the same unique signature at different times and that store different data).

Each of first file 401 and second file 403 may include a common key or a common field with data that changes and that defines a relationship between the key or field in the different files. Alternatively, each of first file 401 and second file 403 may include a common data type (e.g., commonly formatted data) that is represented in each of first file 401 and second file 403 with different values or changing data. In some embodiments, the changing data may correspond to a timestamp. The timestamps may identify different times at which files 401 and 403 and/or data for files 401 and 403 was generated. The relationship between the timestamps may have significance when the files include images that identify a change, and the timestamps provide a measure associated with the change. For instance, the timestamps may be used to determine the rate of change, amount of change per unit of time, and/or other like measures.

Controller 103 may assign (at 404) first file 401 to first anonymization agent 105-1, and second file 403 to second anonymization agent 105-2 for anonymization of the changing data. Controller 103 may assign (at 404) first file 401 and second file 403 at the same time for parallel or simultaneous anonymization of the files by different anonymization agents 105-1 and 105-2.

First anonymization agent 105-1 may scan (at 406) first file 401 to determine that first file 401 contains a data type for changing data and/or that the changing data is of a variable data type. For instance, first anonymization agent 105-1 may use a regular expression to determine that the changing data in first file 401 is formatted according to a time data type, and therefore corresponds to a timestamp. Accordingly, first anonymization agent 105-1 may issue (at 408) a first query with a unique signature, that is derived from the data of first file 401, and an identifier for the time data type.

In response to the first query and further in response to determine that no offset or fuzz criteria has been created for the unique signature and/or time data type, database 107 may use a random number generator to create (at 410) a unique time offset by which to anonymize the time data type in first file 401, second file 403, and/or all files in the related set of files with the same unique signature. Database 107 may also generate (at 410) fuzz criteria. In some embodiments, the fuzz criteria may include a range by which the offset may be increased or decreased in the related set of files (e.g., file 401, file 403, and/or other files with the same unique signature) without losing the overall relationship between the anonymized timestamps in the different files. In embodiments, the fuzz criteria may be a fractional value of the offset. For instance, if the offset is 1 hour and 6 minutes (e.g., 76 minutes) the fuzz criteria may be +/−76 seconds (10% of the offset).

Database 107 may provide (at 412) the generated offset and fuzz criteria for the time data type of files bearing the particular unique signature to first anonymization agent 105-1, that performs the anonymization of first file 401. Database 107 may create an entry to store the generated offset and fuzz criteria for the time data type of files bearing the particular unique signature, and may provide (at 416) the same offset and fuzz criteria in response to second anonymization agent 105-2 querying (at 414) for the persistent offset to apply to the same time data type for second file 403 having the same particular unique signature as first file 401.

First anonymization agent 105-1 may increase the particular timestamp in first file 401 by 1 hour and 6 minutes (e.g., 76 minutes) based on the offset provided by database 107, and may decrease the resulting value by 1 minute and 8 seconds based on the fuzz criteria specifying a maximum adjustment (e.g., increase or decrease) of 76 seconds. First anonymization agent 105-1 may anonymize other restricted data in first file 401 before outputting (at 418) first anonymized file 405 with the anonymized changing data to database 107 or another destination.

Second anonymization agent 105-2 may anonymize the particular timestamp of second file 403 at the same time as first anonymization agent 105-1 anonymizes first file 401. Second anonymization agent 105-2 may increase the particular timestamp in second file 403 by 1 hour and 16 minutes based on the offset provided by database 107, and may increase the resulting value by 10 second based on the fuzz criteria. Second anonymization agent 105-2 may anonymize other restricted data in second file 403 before outputting second anonymized file 407 with the anonymized changing data to database 107 or another destination.

In this manner, anonymization system 101 may anonymize the changing date in a related set of files in a manner that prevents a bad actor from discovering the original values for the changing data while preserving the actual timing relationship between the timestamps in the related set of files. Moreover, the persistent anonymization of the changing data may be performed in the distributed and stateless manner illustrated in FIG. 4.

As noted above, anonymization system 101 may persistently anonymize the data for restricted data types regardless of the position or ordering of the restricted data types in a related set of files. In some embodiments, anonymization system 101 may identify the restricted data types based on tags that precede, identify, and/or are otherwise associated with the data. In some embodiments, the tags indicate the formatted data that is to follow. For instance, data encoded as part of the DICOM file format may be preceded with a "(XXXX, YYYY)" tag. The XXXX component of the DICOM tag may identify the tag group, and the YYYY component of the DICOM tag may identify the group element. From these tags, anonymization system 101 may identify the patient name, patient age, physician name, and/or other data that is encoded in the DICOM file, and may further identify how each of the different data elements are formatted in the DICOM file.

The data type tags may be defined in a file format definition. Anonymization system 101 may receive and/or store a file format definition for each file format that may be anonymized by anonymization system 101. Anonymization system 101 may select the correct file format definition for a particular file based on extension, encoding, header information, and/or other attributes of the particular file.

In some embodiments, the file format definition may list each of the data type tags, and may provide the formatting for the data of each listed data type. In some embodiments, the file format definition may provide one or more regular expressions, rules, and/or other expressions for identifying the data types (e.g., tags) and/or the formatting of data for different data types. For instance, the DICOM file format may specify an age or date data type as a string of characters with one of the following formats: nnnD, nnnW, nnnM, nnnY; where nnn shall contain the number of days for D, weeks for W, months for M, or years for Y. Accordingly, anonymization system 101 may detect data of different data types strictly from the data formatting, and/or from tags that precede the data and that identify the data type for the data.

Anonymization system 101 may incorporate the file format definition in the anonymization methodology. In some embodiments, controller 103 may receive a file for anonymization, may determine the file format based on the file extension, metadata, and/or other attributes of the file, may select the file formation definition for the identified file format from a plurality of file format definitions, and may provide the file along with the selected file formation definition to an anonymization agent 105.

Anonymization agent 105 may perform regular expression and/or tag matching to identify the data types and/or the associated data within the file that is subject to anonymization. By using the regular expression and/or tag matching, anonymization system 101 may anonymize restricted data that may not be associated with an identifying key, identifier, and/or other value, and may anonymize restricted data anywhere in the file in any order. In other words, anonymization system 101 may anonymize the data of a set of related files that do not follow a fixed placement, positioning, and/or ordering for the data.

In some embodiments, anonymization system 101 may take advantage of tagged data by using a variable encoding of the tags. In particular, the variable encoding may include optimizing, compressing, and/or otherwise modifying the tags that identify the data types of the formatted data and/or the data that is associated with each tag. In actual testing, the variable encoding of the tags provided between a 50% and 75% reduction in tag size, and up to 23 times faster accessing of the data relative to the original tag encoding. These and other performance improvements resulting from the variable encoding of the tag improve overall performance of anonymization system 101 by reducing the overall time for anonymizing the data, reducing the time to access and/or retrieve specific data or a set of data from the file (e.g., original and anonymized), and/or reducing the file size to optimize the file for transfer across data networks.

Figure 5:
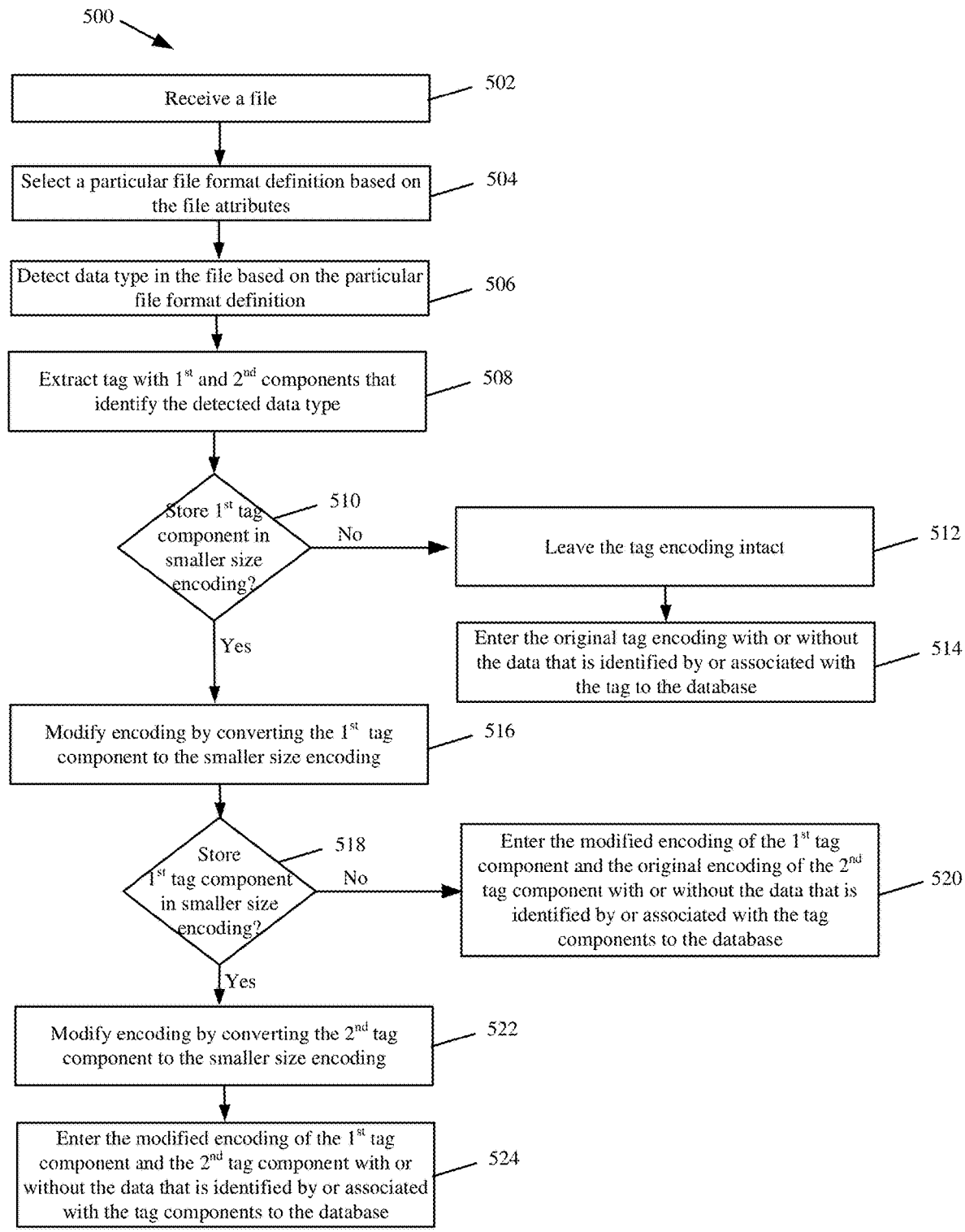
FIG. 5 presents a process for variable encoding of file tags in accordance with some embodiments presented herein.

FIG. 5 presents a process 500 for the variable encoding of file tags in accordance with some embodiments presented herein. Process 500 may be performed by anonymization system 101 and/or its various components such as controller 103 or anonymization agents 105. The variable encoding of process 500 is described relative to the DICOM file format and/or other file formats with the "(XXXX, YYYYY)" defined structure and/or other fixed structure for the data type tags. However, the variable encoding of process 500 may be adapted and applied to other file formats that have different fixed or variable structures for data type tags.

Process 500 may include receiving (at 502) a file, and selecting (at 504) a particular file format definition from a plurality of file format definitions based on the file extension, metadata, and/or other attributes of the file. The particular file format definition may specify the regular expressions or tags from which anonymization system 101 may determine the data types of different data based on the formatting of the data or the data type of data that follows a particular tag. The data types may be used to differentiate restricted data from unrestricted data. For instance, a patient name data type may correspond to restricted data that requires anonymization, whereas an institution address data type may correspond to unrestricted data that does not require anonymization. In some embodiments, the selected particular file format definition may differentiate and/or flag the tags for restricted data types from the tags for unrestricted data types. The DICOM file format definition may specify hundreds of supported data types via tags defined according to the "(XXXX, YYYY)" format.

In some embodiments, controller 103 may receive (at 502) the file, and may select (at 504) the particular file format definition. Controller 103 may provide the file with the particular file format definition to a particular anonymization agent 105.

Process 500 may include detecting (at 506) data types in the file based on the particular file format definition. To detect (at 506) the data types, the particular anonymization agent 105 may perform regular expression and/or tag matching based on regular expressions and/or tags from the particular file format definition.

Process 500 may include extracting (at 508) the tag for the detected data type. As noted above, the DICOM file format defines tags using the "(XXXX, YYYY)" format with each of the XXXX and YYYY components encoded as a different unsigned integer 16 ("UInt16") (e.g., a variable type with a size that supports values ranging between 0 and 65,535). Each UInt16 may consume 2 bytes. Alternatively, the tags may be defined as a character string in which each character is 1 byte in size. A string representation of a DICOM tag would therefore consume 8 bytes (e.g., XXXXYYYY). In any case, extracting (at 508) the tag may include parsing the tag into a first tag component (e.g., XXXX) and a second tag component (e.g., YYYY).

Process 500 may include inspecting the extracted tag to determine (at 510) whether the value of the first tag component exceeds a threshold value. In particular, process 500 may include determining (at 510) whether the encoding of the first tag component can be reduced in size. For instance, process 500 may determine (at 510) if the 2-byte UInt16 encoding for the first tag component stores a value that can be stored in a smaller 1-byte unsigned integer 8 or character encoding. For much of the data and/or data types that are accessed from a DICOM file, the DICOM tag group (e.g., XXXX) may have a value between 0 and 255. The group element (e.g., YYYY) for the corresponding DICOM tag group may have a value in the thousands (e.g., between 0 and 65,535).

In response to determining (at 510—No) that the value for the first tag component of the extracted tag may not be stored using a smaller size encoding, process 500 may include leaving (at 512) the tag encoding intact. Process 500 may include entering (at 514) the original tag encoding with or without the data that is identified by or associated with the tag to database 107 or to an anonymized file that is output by the particular anonymization agent 105. In some embodiments, database 107 may be optimized to store and access strings. Accordingly, in some such embodiments, each byte of the original encoded tag may be converted to a 1-byte character so that the entire tag may be stored as a string. In some embodiments, the particular anonymization agent 105 may determine whether the data associated with the extracted data is subject to anonymization, may enter (at 514) the original tag with the original data into database 107 when the original data or the data type of the original tag is not subject to anonymization, and may enter (at 514) the original tag with anonymized data, instead of the original data, into database 107 when the original data or the data type of the original tag is subject to anonymization. The entry (at 514) of the tag with or without the corresponding data may be performed to accelerate access to the data type and/or data. For instance, if anonymization system 101 receives a query for the data type and/or data, anonymization system 101 may simply identify and access all the data that satisfies the query directly from database 107, rather than scan each and every file for the matching data types or data.

In response to determining (at 510—Yes) that the value for the first tag component of the extracted tag may be stored using a smaller size encoding, process 500 may include modifying (at 516) the tag encoding by converting the first tag component to the smaller size encoding. For instance, if the first tag component of the extracted tag is a 2-byte UInt16 that stores a value of 16, the particular anonymization agent 105 may replace the 2-byte UInt16 with a 1-byte UInt8 variable or data structure, and may store the value of 16 in the 1-byte UInt8 variable or data structure. Alternatively, the particular anonymization agent 105 may recast the 2-byte UInt16 to the 1-byte UInt8. Process 500 may include determining (at 518) whether the encoding of the second tag component can be reduced in size.

In response to determining (at 518—No) that the value for the second tag component of the extracted tag may not be stored using a smaller size encoding, process 500 may include entering (at 520) the modified encoding of the first tag component and the original encoding of the second tag component with or without the data that is identified by or associated with the first and second tag components to database 107. In response to determining (at 518—Yes) that the value for the second tag component of the extracted tag may be stored using a smaller size encoding, process 500 may include modifying (at 522) the tag encoding by converting the second tag component to the smaller size encoding, and entering (at 524) the modified encoding of the first tag component and the second component with or without the data that is identified by or associated with the first and second tag components to database 107 or to an anonymized file that is output by the particular anonymization agent 105.

Process 500 may continue until the variable encoding is performed for all data types in the received file. Accordingly, process 500 may detect (at 506) a next data type in the file until all data types in the file have been identified and processed via the variable encoding recited in operations 508-524.

Anonymization system 101 may respond to user queries for the anonymized data based on the variable encoded tags. Since the variable encoded tags consume less memory or space than the original encoded tags, anonymization system 101 is able to search the variable encoded tags in less time than the original encoded tags. Consequently, anonymization system 101 may generate responses to user queries with anonymized data and/or other requested data in less time using the variable encoded tags than the original encoded tags.

Moreover, anonymization system 101 may transfer the anonymized file with the variable encoded tags to a destination in less time than the anonymized file with the original encoded tags due to the reduction in the file size that results from storing the anonymized data with the variable encoded tags instead of the larger original encoded tags.

Figure 6:
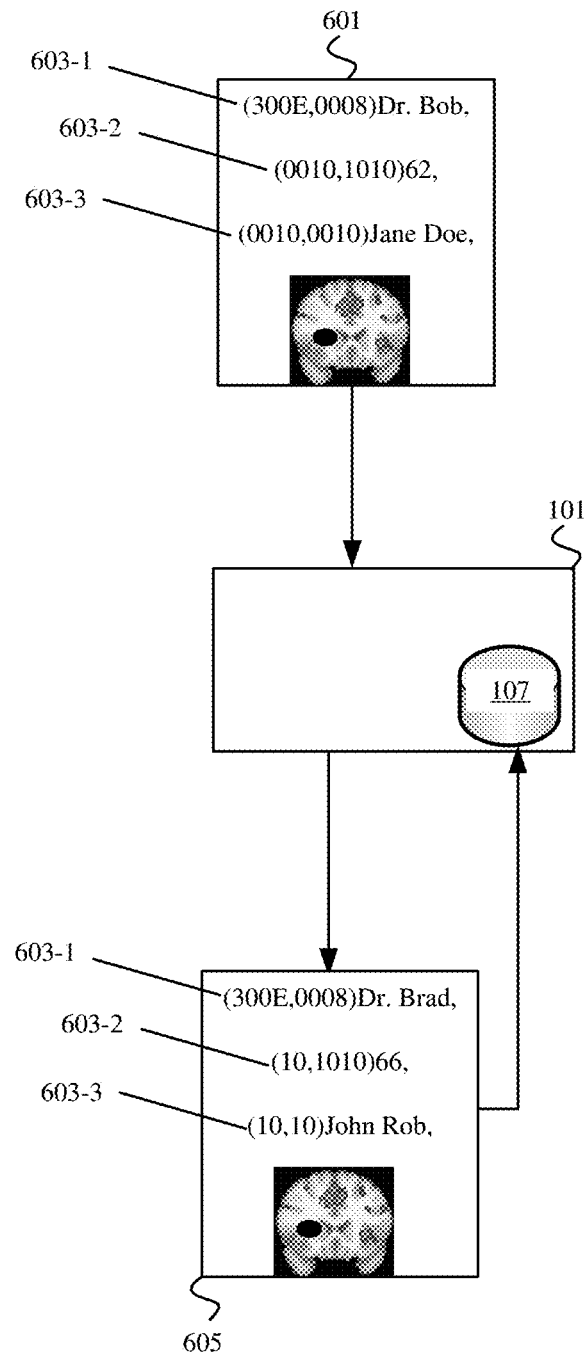
FIG. 6 illustrates examples of the file size reduction resulting from the variable encoding that is performed by the anonymization system in accordance with some embodiments presented herein.

FIG. 6 illustrates examples of the file size reduction resulting from the variable encoding that is performed by anonymization system 101 in accordance with some embodiments presented herein. As shown in FIG. 6, anonymization system 101 may receive original file 601 that includes data elements 603-1, 603-2, and 603-3 (sometimes collectively referred to as "data elements 603" or individually as "data element 603"). Each data element 603 may include a tag with a first 2-byte tag component and a second 2-byte tag, and data that is formatted according to the data type identified by the corresponding tag. Moreover, the data from each of data elements 603 may be subject to anonymization.

Anonymization system 101 may determine that the first tag component of first data element 603-1 has a value that is greater than 255 or a 1-byte encoding. For instance, the first tag of first data element 603-1 may have a value of 12,302 (e.g., hexadecimal value of 300E) for identifying a reviewer name in the DICOM file format. Accordingly, anonymization system 101 may retain the encoding for first data element 603-1, may generate an anonymized representation for the data of first data element 603-1, and/or may enter the original encoded tag and the anonymized first data to database 107 or to anonymized file 605.

Anonymization system 101 may determine that the first tag component of second data element 603-2 has a value that is less than 255 or a 1-byte encoding, and that the second tag component of second data element 603-2 has a value that is greater than 255 or a 1-byte encoding. For instance, the first tag component of second data element 603-2 may a have value of 16 (e.g., hexadecimal value of 0010), and the second tag component of second data element 603-2 may have a value of 4,112 (e.g., hexadecimal value of 1010) to collectively identify the patient's age in the DICOM file format. Anonymization system 101 may modify the encoding of second data element 603-2 by converting the first tag component from a UInt16 or 2-byte encoding to a UInt8 or 1-byte encoding, may retain the original encoding of the second tag component for second data element 603-2, may generate an anonymized representation for the data of second data element 603-2, and/or may enter the variable encoded tag and the anonymized second data to database 107 or to anonymized file 605.

Anonymization system 101 may determine that the first tag component and the second tag component of third data element 603-3 each have a value that is less than 255 or a 1-byte encoding. For instance, the first tag component of third data element 603-3 may a have value of 16, and the second tag component of third data element 603-3 may have a value of 16 to collectively identify the patient's name in the DICOM file format. Anonymization system 101 may modify the encoding of third data element 603-3 by converting each of the first tag component and the second tag component from a UInt16 or 2-byte encoding to a UInt8 or 1-byte encoding, may generate an anonymized representation for the data of third data element 603-3, and/or may enter the variable encoded tag and the anonymized third data to database 107 or to anonymized file 605.

In some embodiments, anonymization system 101 and/or database 107 may decode the variable encoded tags back to their original encoding in order to output data to a device that interprets the data (e.g., anonymized data and/or original data) based on the originally encoded tag (e.g., the format for the corresponding data type in the particular file format definition). The decoding time may be insignificant and may add no penalty because casting from a smaller variable to a larger variable (e.g., from a UInt8 to a UInt16) requires no processing effort, and/or may be performed by simply allocating additional memory.

Figure 7:
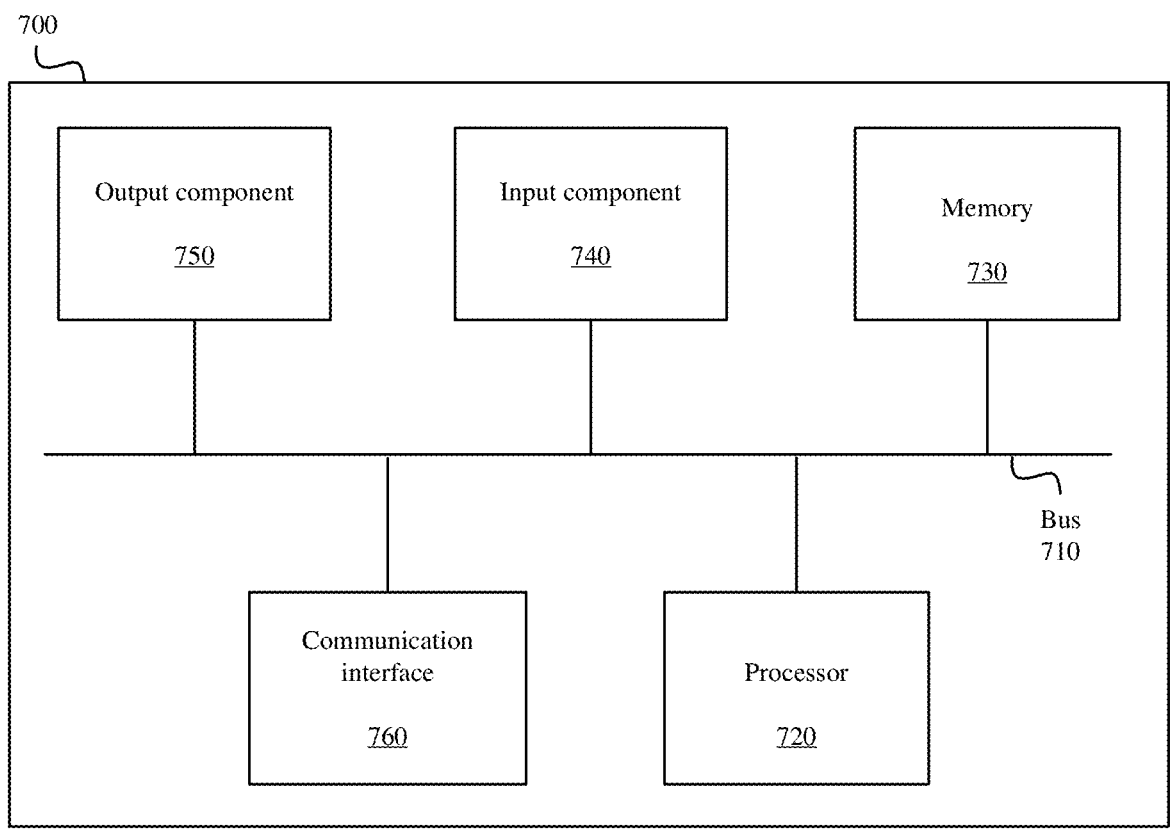
FIG. 7 illustrates example components of one or more devices, according to one or more embodiments described herein.

FIG. 7 is a diagram of example components of device 700. Device 700 may be used to implement one or more of the devices or systems described above (e.g., anonymization system 101, controller 103, anonymization agent 105, database 107, etc.). Device 700 may include bus 710, processor 720, memory 730, input component 740, output component 750, and communication interface 760. In another implementation, device 700 may include additional, fewer, different, or differently arranged components.

Bus 710 may include one or more communication paths that permit communication among the components of device 700. Processor 720 may include a processor, microprocessor, or processing logic that may interpret and execute instructions. Memory 730 may include any type of dynamic storage device that may store information and instructions for execution by processor 720, and/or any type of non-volatile storage device that may store information for use by processor 720.

Input component 740 may include a mechanism that permits an operator to input information to device 700, such as a keyboard, a keypad, a button, a switch, etc. Output component 750 may include a mechanism that outputs information to the operator, such as a display, a speaker, one or more light emitting diodes ("LEDs"), etc.

Communication interface 760 may include any transceiver-like mechanism that enables device 700 to communicate with other devices and/or systems. For example, communication interface 760 may include an Ethernet interface, an optical interface, a coaxial interface, or the like. Communication interface 760 may include a wireless communication device, such as an infrared ("IR") receiver, a Bluetooth® radio, or the like. The wireless communication device may be coupled to an external device, such as a remote control, a wireless keyboard, a mobile telephone, etc. In some embodiments, device 700 may include more than one communication interface 760. For instance, device 700 may include an optical interface and an Ethernet interface.

Device 700 may perform certain operations relating to one or more processes described above. Device 700 may perform these operations in response to processor 720 executing software instructions stored in a computer-readable medium, such as memory 730. A computer-readable medium may be defined as a non-transitory memory device. A memory device may include space within a single physical memory device or spread across multiple physical memory devices. The software instructions may be read into memory 730 from another computer-readable medium or from another device. The software instructions stored in memory 730 may cause processor 720 to perform processes described herein. Alternatively, hardwired circuitry may be used in place of or in combination with software instructions to implement processes described herein. Thus, implementations described herein are not limited to any specific combination of hardware circuitry and software.

The foregoing description of implementations provides illustration and description, but is not intended to be exhaustive or to limit the possible implementations to the precise form disclosed. Modifications and variations are possible in light of the above disclosure or may be acquired from practice of the implementations.

The actual software code or specialized control hardware used to implement an embodiment is not limiting of the embodiment. Thus, the operation and behavior of the embodiment has been described without reference to the specific software code, it being understood that software and control hardware may be designed based on the description herein.

For example, while series of messages, blocks, and/or signals have been described with regard to some of the above figures, the order of the messages, blocks, and/or signals may be modified in other implementations. Further, non-dependent blocks and/or signals may be performed in parallel. Additionally, while the figures have been described in the context of particular devices performing particular acts, in practice, one or more other devices may perform some or all of these acts in lieu of, or in addition to, the above-mentioned devices.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

Further, while certain connections or devices are shown, in practice, additional, fewer, or different, connections or devices may be used. Furthermore, while various devices and networks are shown separately, in practice, the functionality of multiple devices may be performed by a single device, or the functionality of one device may be performed by multiple devices. Further, while some devices are shown as communicating with a network, some such devices may be incorporated, in whole or in part, as a part of the network.

To the extent the aforementioned embodiments collect, store or employ personal information provided by individuals, it should be understood that such information shall be used in accordance with all applicable laws concerning protection of personal information. Additionally, the collection, storage and use of such information may be subject to consent of the individual to such activity, for example, through well-known "opt-in" or "opt-out" processes as may be appropriate for the situation and type of information. Storage and use of personal information may be in an appropriately secure manner reflective of the type of information, for example, through various encryption and anonymization techniques for particularly sensitive information.

Some implementations described herein may be described in conjunction with thresholds. The term "greater than" (or similar terms), as used herein to describe a relationship of a value to a threshold, may be used interchangeably with the term "greater than or equal to" (or similar terms). Similarly, the term "less than" (or similar terms), as used herein to describe a relationship of a value to a threshold, may be used interchangeably with the term "less than or equal to" (or similar terms). As used herein, "exceeding" a threshold (or similar terms) may be used interchangeably with "being greater than a threshold," "being greater than or equal to a threshold," "being less than a threshold," "being less than or equal to a threshold," or other similar terms, depending on the context in which the threshold is used.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items, and may be used interchangeably with the phrase "one or more." Where only one item is intended, the terms "one," "single," "only," or similar language is used. Further, the phrase "based on" is intended to mean "based, at least in part, on" unless explicitly stated otherwise.

What is claimed is:

1. A method comprising:
   receiving a first file comprising at least a first data element, the first data element comprising a tag and restricted data, wherein the tag identifies a format of the restricted data;
   changing a first encoding of the tag having a first size to a second encoding having a second size that is smaller than the first size;
   determining that one or more of the tag or a format of the restricted data corresponds to a static data type;
   generating a persistent mapping by selecting anonymized data from a plurality of anonymized data using a hash of one or more of the restricted data or a unique signature of the first file;
   replacing the restricted data with the anonymized data based on the persistent mapping of the restricted data to the anonymized data; and
   outputting the first data element with the second encoding of the tag and the anonymized data to a database or an anonymized second file.

2. The method of claim 1 further comprising:
   receiving a third file comprising at least a second data element, the second data element comprising the tag and the restricted data of the first data element;
   generating a unique signature based on one or more data elements of the third file;
   retrieving the persistent mapping of the restricted data to the anonymized data based on a query comprising the unique signature of the third file and the tag, and further based on the unique signature of the third file matching the unique signature of the first file; and
   outputting the second data element with the second encoding of the tag and the anonymized data to the database or an anonymized fourth file.

3. The method of claim 1 further comprising:
   receiving a third file comprising at least a second data element, the second data element comprising the tag and second data that is different than the restricted data of the first data element;
   generating a unique signature based on one or more data elements of the third file;
   retrieving the persistent mapping of the restricted data to the anonymized data based on a query comprising the unique signature of the third file and the tag, and further based on the unique signature of the third file matching the unique signature of the first file;
   adjusting the second data by an offset value that was previously used to change from the restricted data to the anonymized data, wherein the offset is defined as part of the persistent mapping; and
   outputting the second data element with the second encoding of the tag and the second data modified by the offset value to the database or an anonymized fourth file.

4. The method of claim 3, wherein adjusting the second data further comprises:

performing a second adjustment of the second data using fuzz criteria after modifying the second data by the offset value, wherein performing the second adjustment comprises:
- randomly selecting a particular value within a range of values specified as the fuzz criteria; and
- modifying the second data by the offset value and the particular value.

5. The method of claim 4, wherein performing the second adjustment comprises:
- providing different offsets to the restricted data and the second data while preserving a time relationship between the anonymized data and the second data modified by the offset value and the particular value.

6. The method of claim 1, wherein changing the first encoding comprises:
- parsing the tag into at least a first tag component that is encoded using a first variable type, and a second tag component that is encoded using the first variable type;
- determining a value of the first tag component is less than a threshold value, and a value of the second tag component is greater than the threshold value;
- recasting the first tag component from the first variable type to a second variable type that consumes less memory than the first variable type; and
- generating the second encoding of the tag with the second variable type for the first tag component, and the first variable type for the second tag component.

7. The method of claim 1, wherein changing the first encoding comprises:
- parsing the tag into at least a first tag component that is encoded using a first variable type, and a second tag component that is encoded using the first variable type;
- determining that a value of the first tag component and a value of the second tag component is within a range of values supported by a different second variable type that consumes less memory than the first variable type; and
- generating the second encoding of the tag with the second variable type for the first tag component and the second tag component.

8. The method of claim 1 further comprising:
- assigning the first file to a first anonymization agent for anonymization;
- receiving a third file comprising at least a second data element, the second data element comprising the tag and the restricted data of the first data element;
- assigning the third file to a different second anonymization agent that runs in parallel with the first anonymization agent;
- identifying the persistent mapping based on one or more data elements of the third file; and
- using the second anonymization agent to replace the restricted data of the second data element at a same time period as the first anonymization agent replacing the restricted data of the first data element with the anonymized data.

9. The method of claim 1, wherein the tag is a first tag, the method further comprising:
- determining that the first file comprises a second data element with a different second tag and different second data;
- determining that one or more of the second tag or a format of the second data corresponds to a changing data type; and
- defining an offset value and fuzz criteria in response to determining the changing data type and one or more of the unique signature of the first file and the second tag not being associated with any offset value or fuzz criteria; and
- anonymizing the second data using the offset value and a randomly selected value within a range of values of the fuzz criteria.

10. The method of claim 9 further comprising:
- performing a persistent replacement of the restricted data with the anonymized data in a plurality of files in response to each of the plurality of files comprising the tag of the first data element and a unique signature that matches the unique signature of the first file; and
- offsetting different values that are stored with the second tag in the plurality of files with the same offset value and a different randomly selected value within the range of values of the fuzz criteria in response to each of the plurality of files comprising the second tag and the unique signature that matches the unique signature of the first file.

11. The method of claim 1 further comprising:
- receiving a plurality of files;
- determining a load associated with anonymizing the plurality of files;
- distributing different sets of the plurality of files to different anonymization agents; and
- anonymizing restricted data in each set of files with a different anonymization agent.

12. A system comprising:
one or more processors configured to:
- receive a first file comprising at least a first data element, the first data element comprising a tag and restricted data, wherein the tag identifies a format of the restricted data;
- change a first encoding of the tag having a first size to a second encoding having a second size that is smaller than the first size;
- determine that one or more of the tag or a format of the restricted data corresponds to a static data type;
- generate a persistent mapping by selecting anonymized data from a plurality of anonymized data using a hash of one or more of the restricted data or a unique signature of the first file;
- replace the restricted data with the anonymized data based on the persistent mapping of the restricted data to the anonymized data; and
- output the first data element with the second encoding of the tag and the anonymized data to a database or an anonymized second file.

13. The system of claim 12, wherein the one or more processors are further configured to:
- receive a third file comprising at least a second data element, the second data element comprising the tag and the restricted data of the first data element;
- generate a unique signature based on one or more data elements of the third file;
- retrieve the persistent mapping of the restricted data to the anonymized data based on a query comprising the unique signature of the third file and the tag, and further based on the unique signature of the third file matching the unique signature of the first file; and
- output the second data element with the second encoding of the tag and the anonymized data to the database or an anonymized fourth file.

14. The system of claim 12, wherein the one or more processors are further configured to:

receive a third file comprising at least a second data
   element, the second data element comprising the tag
   and second data that is different than the restricted data
   of the first data element;
generate a unique signature based on one or more data
   elements of the third file;
retrieve the persistent mapping of the restricted data to the
   anonymized data based on a query comprising the
   unique signature of the third file and the tag, and further
   based on the unique signature of the third file matching
   the unique signature of the first file;
adjust the second data by an offset value that was previously used to change from the restricted data to the
   anonymized data, wherein the offset is defined as part
   of the persistent mapping; and
output the second data element with the second encoding
   of the tag and the second data modified by the offset
   value to the database or an anonymized fourth file.

15. The system of claim 14, wherein the one or more processors are further configured to:
   perform a second adjustment of the second data using fuzz criteria after modifying the second data by the offset value, wherein performing the second adjustment comprises:
      randomly selecting a particular value within a range of values specified as the fuzz criteria; and
      modifying the second data by the offset value and the particular value.

16. The system of claim 12, wherein the one or more processors are further configured to:
   parse the tag into at least a first tag component that is encoded using a first variable type, and a second tag component that is encoded using the first variable type;
   determine a value of the first tag component is less than a threshold value, and a value of the second tag component is greater than the threshold value;
   recast the first tag component from the first variable type to a second variable type that consumes less memory than the first variable type; and
   generate the second encoding of the tag with the second variable type for the first tag component, and the first variable type for the second tag component.

17. The system of claim 12, wherein the one or more processors are further configured to:
   assign the first file to a first anonymization agent for anonymization;
   receive a third file comprising at least a second data element, the second data element comprising the tag and the restricted data of the first data element;
   assign the third file to a different second anonymization agent that runs in parallel with the first anonymization agent;
   identify the persistent mapping based on one or more data elements of the third file; and
   use the second anonymization agent to replace the restricted data of the second data element at a same time period as the first anonymization agent replacing the restricted data of the first data element with the anonymized data.

18. A method comprising:
   receiving a first file comprising at least a first data element, the first data element comprising a tag and restricted data, wherein the tag identifies a format of the restricted data;
   changing a first encoding of the tag having a first size to a second encoding having a second size that is smaller than the first size;
   replacing the restricted data with different anonymized data based on a persistent mapping of the restricted data to the anonymized data;
   outputting the first data element with the second encoding of the tag and the anonymized data to a database or an anonymized second file;
   receiving a third file comprising at least a second data element, the second data element comprising the tag and second data that is different than the restricted data of the first data element;
   generating a unique signature of the third file based on one or more data elements of the third file;
   retrieving the persistent mapping of the restricted data to the anonymized data based on a query comprising the unique signature of the third file and the tag, and further based on the unique signature of the third file matching the unique signature of the first file;
   adjusting the second data by an offset value that was previously used to change from the restricted data to the anonymized data, wherein the offset is defined as part of the persistent mapping; and
   outputting the second data element with the second encoding of the tag and the second data modified by the offset value to the database or an anonymized fourth file.

19. A system comprising:
   one or more processors configured to:
      receive a first file comprising at least a first data element, the first data element comprising a tag and restricted data, wherein the tag identifies a format of the restricted data;
      change a first encoding of the tag having a first size to a second encoding having a second size that is smaller than the first size;
      replace the restricted data with different anonymized data based on a persistent mapping of the restricted data to the anonymized data;
      output the first data element with the second encoding of the tag and the anonymized data to a database or an anonymized second file;
      receive a third file comprising at least a second data element, the second data element comprising the tag and second data that is different than the restricted data of the first data element;
      generate a unique signature of the third file based on one or more data elements of the third file;
      retrieve the persistent mapping of the restricted data to the anonymized data based on a query comprising the unique signature of the third file and the tag, and further based on the unique signature of the third file matching the unique signature of the first file;
      adjust the second data by an offset value that was previously used to change from the restricted data to the anonymized data, wherein the offset is defined as part of the persistent mapping; and
      output the second data element with the second encoding of the tag and the second data modified by the offset value to the database or an anonymized fourth file.

20. A method comprising:
   receiving a first file comprising at least a first data element, the first data element comprising a tag and restricted data, wherein the tag identifies a format of the restricted data;
   changing a first encoding of the tag having a first size to a second encoding having a second size that is smaller than the first size;

replacing the restricted data with different anonymized data based on a persistent mapping of the restricted data to the anonymized data;

outputting the first data element with the second encoding of the tag and the anonymized data to a database or an anonymized second file;

receiving a plurality of files;

determining a load associated with anonymizing the plurality of files;

distributing different sets of the plurality of files to different anonymization agents; and anonymizing restricted data in each of the different sets of files with a different anonymization agent.

21. A system comprising:

one or more processors configured to:

receive a first file comprising at least a first data element, the first data element comprising a tag and restricted data, wherein the tag identifies a format of the restricted data;

parse the tag into at least a first tag component that is encoded using a first variable type, and a second tag component that is encoded using the first variable type;

determine a value of the first tag component is less than a threshold value, and a value of the second tag component is greater than the threshold value;

recast the first tag component from the first variable type to a second variable type that consumes less memory than the first variable type;

generate a second encoding of the tag with the second variable type for the first tag component, and the first variable type for the second tag component;

replace the restricted data with different anonymized data based on a persistent mapping of the restricted data to the anonymized data; and output the first data element with the second encoding of the tag and the anonymized data to a database or an anonymized second file.

\* \* \* \* \*